United States Patent [19]

Frisbie et al.

[11] Patent Number: 5,246,007
[45] Date of Patent: * Sep. 21, 1993

[54] VASCULAR CATHETER FOR MEASURING FLOW CHARACTERISTICS AND METHOD

[75] Inventors: Jeffrey S. Frisbie, San Jose; Menahem F. Nassi, Palo Alto, both of Calif.

[73] Assignee: Cardiometrics, Inc., Mountain View, Calif.

[*] Notice: The portion of the term of this patent subsequent to Aug. 14, 2007 has been disclaimed.

[21] Appl. No.: 851,207

[22] Filed: Mar. 13, 1992

[51] Int. Cl.⁵ .................................................. A61B 8/12
[52] U.S. Cl. ........................... 128/662.06; 128/661.09; 128/772
[58] Field of Search ................ 128/661.08, 661.09, 128/661.10, 662.06, 772; 604/264, 280

[56] References Cited

U.S. PATENT DOCUMENTS

| 4,802,490 | 2/1989 | Johnston | 128/661.08 |
| 4,947,852 | 8/1990 | Nassi et al. | 128/662.06 |
| 5,058,595 | 10/1991 | Kern | 128/662.06 |
| 5,121,749 | 6/1992 | Nassi et al. | 128/662.06 |

Primary Examiner—William E. Kamm
Assistant Examiner—George Manuel
Attorney, Agent, or Firm—Flehr, Hohbach, Test, Albritton & Herbert

[57] ABSTRACT

Vascular catheter for measuring flow characteristics of a liquid in a vessel having a wall and an axis extending longitudinally of the vessel parallel to the vessel wall comprising a flexible elongate tubular member adapted to be introduced into the vessel and having proximal and distal extremities. The flexible elongate member has a lumen extending therethrough. The flexible elongate member has at least one preformed bend thereon adjacent the distal extremity. A plurality of ultrasonic transducers are mounted on the flexible elongate member adjacent to the bend. Conductors are connected to the ultrasonic transducers and extend through the proximal extremity of the flexible elongate tubular member. The flexible elongate member has an opening therein in the distal extremity which is a communication with the lumen.

10 Claims, 4 Drawing Sheets

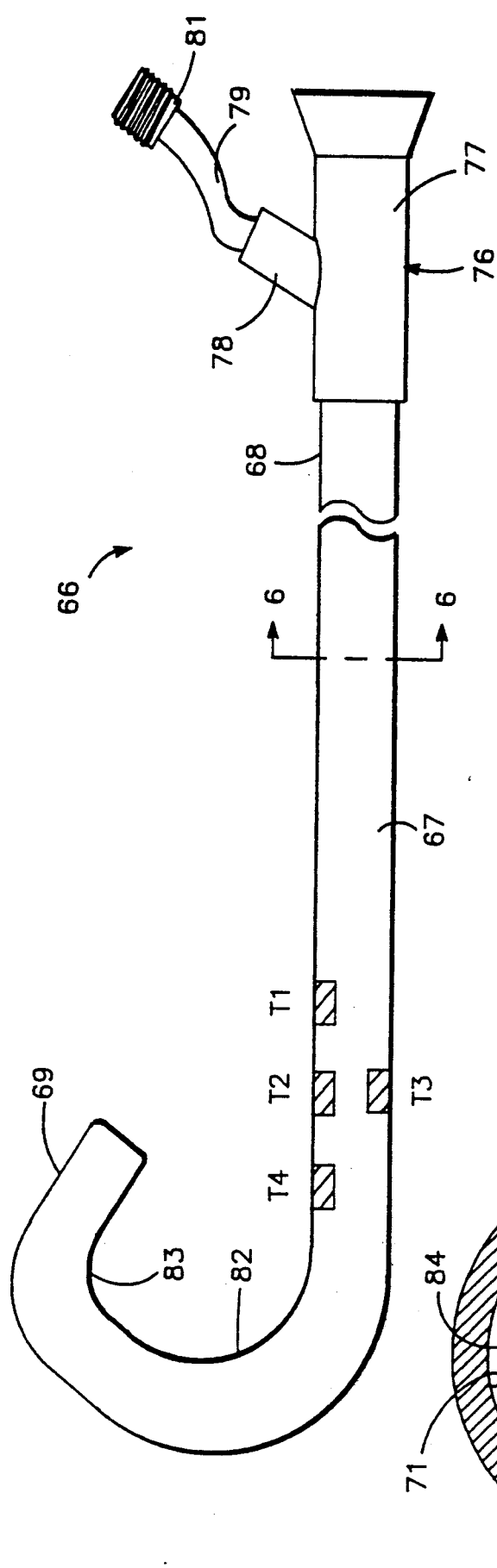

VASCULAR CATHETER FOR MEASURING FLOW CHARACTERISTICS AND METHOD

This invention relates to a vascular catheter for measurement of flow characteristics and method and more particularly to such a catheter which is incorporated into an angiographic catheter or alternatively into a guiding catheter.

Catheters for continuously measuring flow characteristics such as volumetric blood have heretofore been disclosed as for example in U.S. Pat. No. 4,947,852 and 5,078,148. The catheter disclosed in the '852 patent is particularly adapted for use in the right side of the heart in the pulmonary artery. It is provided with a latex balloon which when inflated is adapted to plug the pulmonary artery in which the catheter is disposed. During cardiac catheterization laboratory procedures on the left or high pressure side of the heart, such as coronary angiography. It is at times desirable to obtain an assessment of cardiac flow characteristics. In order to obtain these measurements, it is necessary to introduce a catheter such as that disclosed in the '852 patent into the right side of the heart. This requires the use of an additional catheter and an additional physician's time for making such measurements. There is therefore a need for a new and improved vascular catheter for measurement of flow characteristics and method which overcomes these disadvantages.

In general it is an object of the present invention to provide a vascular catheter for the measurement of flow characteristics and a method for evaluating total cardiac output during coronary catheterization.

Another object of the invention is to provide a vascular catheter and method of the above catheter in which substantially the entire blood flow output from the ascending aorta of the human heart is measured.

Another object of the invention is to provide a catheter and method of the above character in which output is measured during systole.

Another object of the invention is to provide a catheter and method of the above character in which separate velocity measurements can be made contemporaneously with flow measurements.

Additional objects and features of the invention will appear from the following description in which the preferred embodiments are set forth in detail in conjunction with the accompanying drawings.

FIG. 5 is a plan view of a vascular catheter made in accordance with the present invention which is particularly applicable in angiographic diagnostic procedures.

FIG. 6 is a cross-sectional view taken along the line 6—6 of FIG. 5.

In general, the present invention is directed to a coronary angiographic or guiding catheter which has ultrasonic transducers mounted on the body of the catheter for measuring blood flow velocities and vessel diameter in the region of the coronary ostium and the aortic arch for the purpose of evaluating total cardiac output during coronary catheterization. The coronary angiographic or guiding catheter is for use for measuring the flow characteristics of a liquid in a vessel having a wall and an axis extending longitudinally of the vessel parallel to the vessel wall. It consists of a flexible elongate member having a lumen extending therethrough and adapted to be introduced into the vessel. The flexible elongate member has proximal and distal extremities. The flexible elongate member has preformed bend adjacent the distal extremity. A plurality of ultrasonic transducers are mounted on the flexible elongate member adjacent to the bend. The lumen in the flexible elongate member is sized so that it can receive an interventional device such as a guide wire extending therethrough and also to receive a balloon device over the wire. The balloon catheter normally will be extended through the lumen and extend beyond the distal extremity of the catheter.

Figure 1:
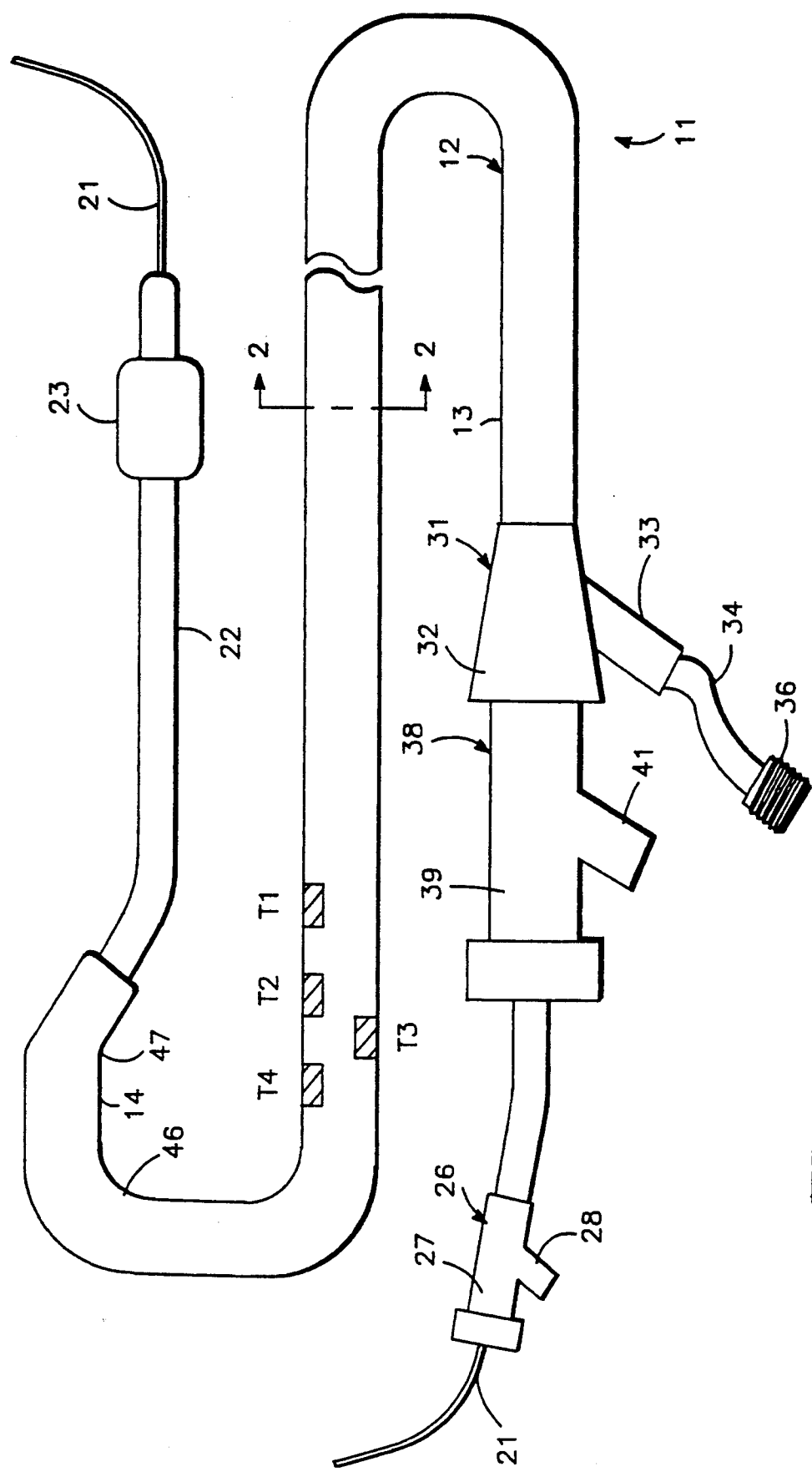
FIG. 1 is a plan view of a vascular catheter for measurement of flow characteristics incorporating the present invention.
Figure 2:
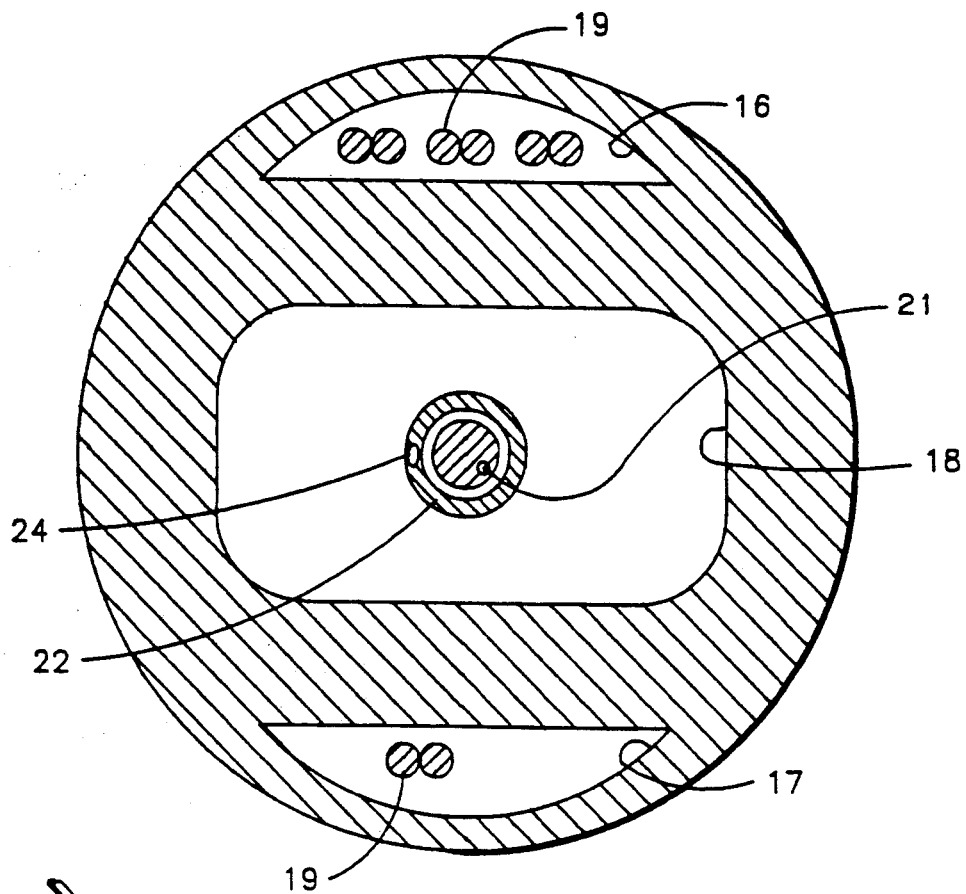
FIG. 2 is a cross-sectional view taken along line 2—2 of FIG. 1.

More in particular, the coronary guiding catheter shown in FIGS. 1 and 2 consists of a flexible elongate tubular member 12 of a suitable material such as plastic. It is provided with proximal and distal extremities 13 and 14. As shown in the cross-sectional view in FIG. 2, the flexible elongate tubular member 12 is provided with first and second crescent-shaped lumens 16 and 17 disposed on opposite sides of a centrally disposed ovoid lumen 18. Lumen 18 can be of a suitable size, as for example, 0.060"×0.080." It is sized so that it can accommodate a guide wire 21 of a conventional type, as for example, one having a diameter of 0.018" and which can receive an over the wire balloon catheter 22 of a conventional type. The catheter 22 is of a length which can extend through the lumen 18 and out through the distal extremity of the flexible elongate tubular member 12 of the guiding catheter 11 as shown in FIG. 1 with the guide wire 21 extending through the balloon catheter 22 and extending forwardly thereof. The balloon catheter 22 is provided with an inflatable balloon 23 which can be inflated through a balloon inflation lumen 24.

The balloon catheter has a suitable diameter, as for example, from 0.040" to 0.055." The crescent-shaped lumens 16 and 17 can have suitable maximum dimensions, as for example, approximately 0.010" and are adapted to receive the conductors 19 for the ultrasonic transducers as hereinafter described. The guiding catheter can be of a suitable size, as for example, from 7 to 11 French and having an outside diameter of 0.091" to 0.143."

It should be noted that the lumen 18 has sufficient space outside of the balloon catheter 22 to permit the introduction of a radiopaque dye in the space between the catheter and the wall of the lumen 18. The proximal extremity of the balloon catheter 22 is provided with a wye adapter 26 having central body 27 and a side arm 28. The side arm 28 is in communication with the balloon inflation lumen 24 and can be utilized for inflating and deflating the balloon 23. A wye adapter 31 is mounted on the proximal extremity 13 of the flexible elongate tubular member 12 and is provided with a main body 32 and a side arm 33. An electrical cable 34 extends from the side arm 33 and is connected to an electrical connector 36.

Another conventional wye connector 38 is mounted in the main body 32 of the wye 31 and is provided with a main body 39 and a side arm 41. The wye 38 is of a conventional type and serves as a hemostasis valve. The side arm 41 can be used for introducing radiopaque liquids through the lumen 18. A predetermined bend or first bend 46 is provided in the distal extremity 14 of the flexible elongate tubular member 12. A plurality of ultrasonic transducers which also can be termed Doppler sensors T1, T2, T3 and T4 are carried by the distal extremity of the catheter near the bend 46. As explained in U.S. Pat. Nos. 4,947,852 and 5,078,148, the sensors or transducers T1-T4 are mounted to obtain velocity and diameter information in the aorta. For example, as shown in FIG. 1, three sensors T1, T2 and T4 can be provided on the front side of the flexible elongate member whereas the other transducer T3 can be provided on the back side of the flexible elongate tubular member 12. The back sensor T3 is used for making a diameter measurement from the flexible elongate tubular member to the wall of the vessel in which it is disposed. Another of the transducers, as for example T1, is used for measuring the velocity and the distance in the other direction of the diameter measurement from the flexible elongate tubular member 12 to the wall of the vessel in which it is disposed. The transducers T2 and T4 are utilized for making first and second velocity measurements as described in U.S. Pat. Nos. 4,947,852 and 5,078,148.

Figure 3B:
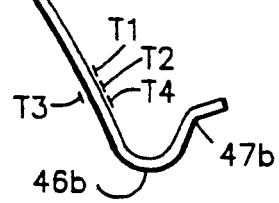
FIGS. 3A, 3B, 3C, 3D and 3E show typical bends which are utilized in the vascular catheter of the present invention for making flow characteristics measurements.
Figure 3A:
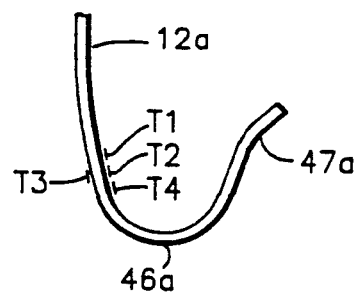
Figure 3C:
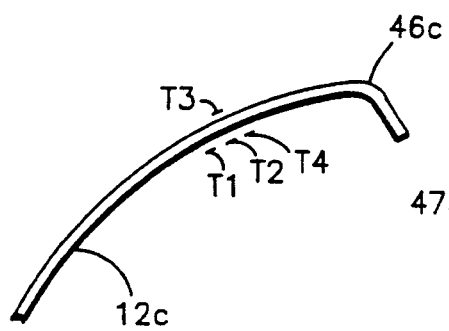
Figure 3D:
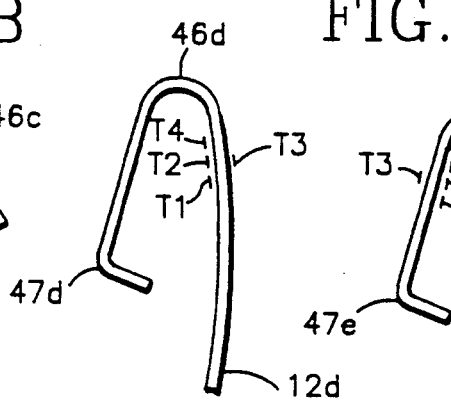
Figure 3E:
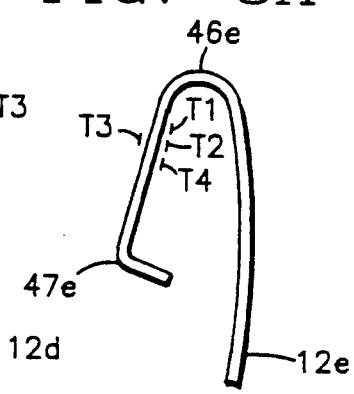

In connection with the present invention it should be appreciated that various types of predetermined bends 46 can be provided in the distal extremity of the flexible elongate tubular member 12. Different bends are shown in FIGS. 3A, 3B, 3C, 3D and 3E. Predetermined bends 46 of conventional types can be placed in the distal extremity of the flexible elongate tubular member 12. As for example as shown in FIG. 3A, a left Amplatz catheter is shown. In FIG. 3B, a right Amplatz catheter and in FIG. 3C a right coronary Judkins catheter are shown. FIG. 3D shows a left coronary Judkins catheter. In FIGS. 3A, 3B, 3C and 3D the three doppler sensors T1, T2 and T4 are mounted on the front side of the catheter adjacent the bend whereas the other doppler sensor T3 is mounted on the rear side. FIG. 3E shows a left coronary Judkins bend which is substantially identical in shape to that shown in FIG. 3D with the exception that the transducers are mounted on the opposite side of the bend 46.

The bends which have been shown in FIGS. 3A through 3E are typical bends for angioplasty guiding catheters and also for angiography catheters. An additional or second predetermined bend 47 is placed in each of the catheters as shown in FIGS. 3A, 3B, 3D, and 3E. These bends which have been identified as 47a, 47b, 47d and 47e can be identified as the second bends from the proximal extremity whereas the bends 46a, 46b, 46c, 46d, and 46e can be considered to be the first bends counting from the proximal extremity of the flexible elongate elements 12a, 12b, 12c, 12d and 12e. The bend is selected in accordance with the part of the anatomy which is to be entered as for example, the right or left coronary tree. In FIG. 3A, 3B, 3C and 3D, the transducers T1, T2, T3 and T4 have been placed on a straight portion of the flexible elongate tubular member 12 proximal to the first bend 46 rather than distal of the first bend 46 as shown in FIG. 3E, the bends being counted from the proximal to the distal extremity of the flexible elongate tubular member 12.

Let it be assumed that it is desired to utilize a guiding catheter 11 and the balloon catheter 22 with a guide wire 21 in connection with the measuring of blood flow velocities and vessel diameter in the region of the coronary ostium and the aortic arch for the purpose of evaluating total cardiac output during coronary catheterization. The guiding catheter 11 is inserted into the femoral artery of the patient by the use of an introducer. Then if believed to be necessary, a conventional guide wire (not shown) 21 can be inserted through the guiding catheter. Both the conventional guide wire and the guiding catheter 11 are advanced through the femoral artery into the descending aorta 51 of the patient and over the aortic arch 52 and past the left subclavian artery 53, the left common carotid artery 54 and the innominate artery 56 and into the ascending aorta 57. The conventional guidewire is then removed. The distal tip 14 of the guiding catheter 11 is positioned in the ostium just distal of the aortic valve 59 so that the coronary tree on either side can be accessed.

Figure 4:
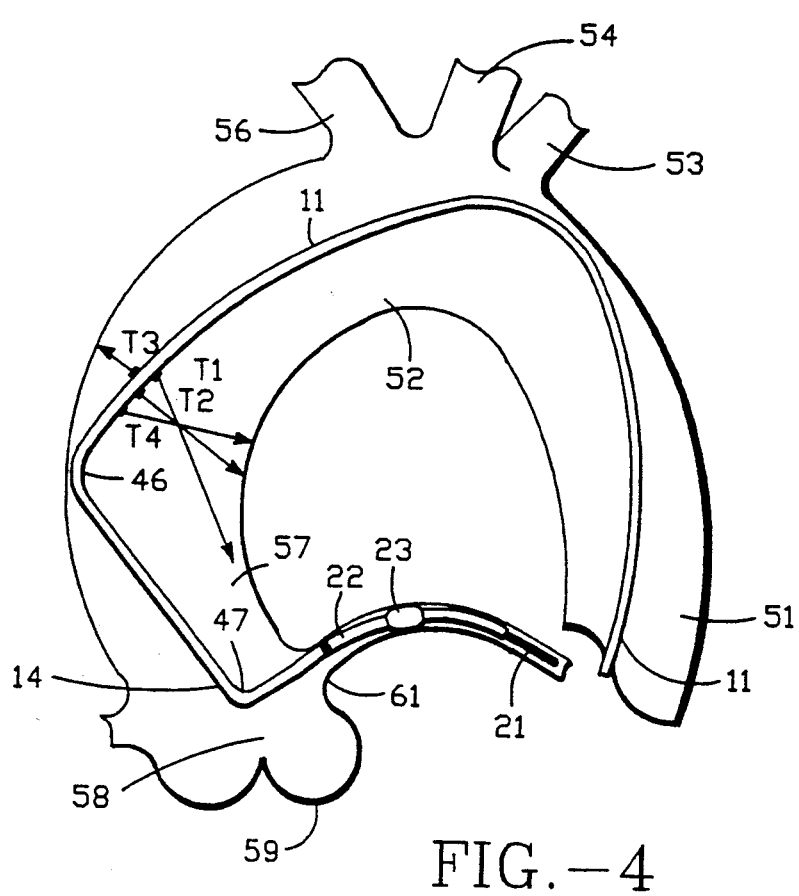
FIG. 4 is a schematic illustration showing the vascular catheter of FIG. 1 of the present invention and the manner in which it is positioned within the heart in accordance with the present method to make volumetric measurements.

Thus as shown in FIG. 4, the left coronary artery 61 is accessed by the distal extremity 14 with the bend 47 of the guiding catheter 11 adjacent thereto. The guiding catheter 11 is disposed in a central plane of the longitudinal axis of the ascending aorta 57 by virtue of placing the catheter adjacent the ostium 58 and in the left coronary artery 61. With the guiding catheter positioned in this manner, the blood flow in the aorta can be measured by connecting the guiding catheter 11 to instrumentation of the type disclosed in U.S. Pat. Nos. 4,947,852 and 5,078,148 in which leads are provided which are connected to the transducers T1, T2, T3 and T4 utilized to measure vessel diameter and velocity as described in said U.S. Pat. Nos. 4,947,852 and 5,078,148.

After the guiding catheter 11 is in the desired position, an initial survey can be accomplished by the use of an angiographic dye introduced through the guiding catheter 11 and viewed fluoroscopically. It can be followed by introducing the guide wire 21 through the guiding catheter followed by the balloon catheter 22 in such a manner so that the distal extremity of the guide wire 21 is advanced ahead of the balloon catheter 22 until the guide wire 21 and balloon catheter 22 have their distal extremities exit from the distal extremity of the guiding catheter 11 into the left coronary artery 61. The balloon catheter 22 can then be utilized for performing a conventional angioplasty to open up a stenosis which has been found within the left coronary artery 61. It should be appreciated that in place of the balloon catheter 22, other medical devices, as for example an atherectomy device may be deployed over the guide wire 21 in place of the balloon catheter 22.

In order to obtain velocity measurements within the left coronary artery 61, the guide wire 21 can be of the type disclosed in U.S. Pat. Nos. 4,958,642 and 4,961,433 which has a Doppler crystal mounted on its distal extremity and connected by conductors extending through the guide wire to conventional instrumentation so that velocity measurements can be made in the left coronary artery 61 at the same time that volumetric blood flow measurements are being made by use of the transducers T1, T2, T3, and T4 on the guiding catheter 11.

After the desired procedures have been performed, the guide wire 21 and the balloon catheter 22 can be removed after deflation of the balloon 23 on the balloon catheter 22 and removal through the guiding catheter. Thereafter the guiding catheter 11 can be removed from the heart and the femoral artery of the patient to complete the procedure.

A coronary angiographic catheter with Doppler capabilities is shown in FIGS. 5 and 6 and as shown therein consists of flexible elongate tubular member 67 formed of a suitable material such as plastic which is provided with proximal and distal extremities 68 and 69. The flexible elongate member 67 has an outside diameter which can range from 0.065" to 0.091." The flexible elongate member 67 is provided with first and second crescent-shaped lumens 71 and 72 and a centrally positioned ovoid lumen 73. The lumens 71 and 72 can have a suitable dimension as for example, approximately 0.010" in any direction extending diametrically of the flexible elongate member 67. The ovoid lumen 73 can have a suitable dimension, as for example, 0.038"×0.060." A wye adapter 76 is mounted on the proximal extremity 68 of the flexible elongate member 67 and is provided with a central body 77 and a side arm 78. A cable 79 extends from the side arm 78 and has an electrical connector 81 provided thereon which is adapted to be connected to a system and apparatus of the type described in U.S. Pat. No. 4,947,852.

The cable 79 is provided with electrical conductors (not shown) that are connected to the ultrasonic or Doppler transducers T1, T2, T3 and T4. The transducers T1-T4 are mounted on the flexible elongate member 67 adjacent the first bend of first and second bends 82 and 83 provided in the distal extremity 69 of the flexible elongate member 67 counting from the proximal to the distal extremity. Conductors 84 in lumens 71 and 72 make contact with the transducer T1, T2, T3 and T4. The distal extremity 69 of the catheter 66 can be provided with different types of bends such as those disclosed in conjunction with the guiding catheter 11 hereinbefore described.

Figure 7:
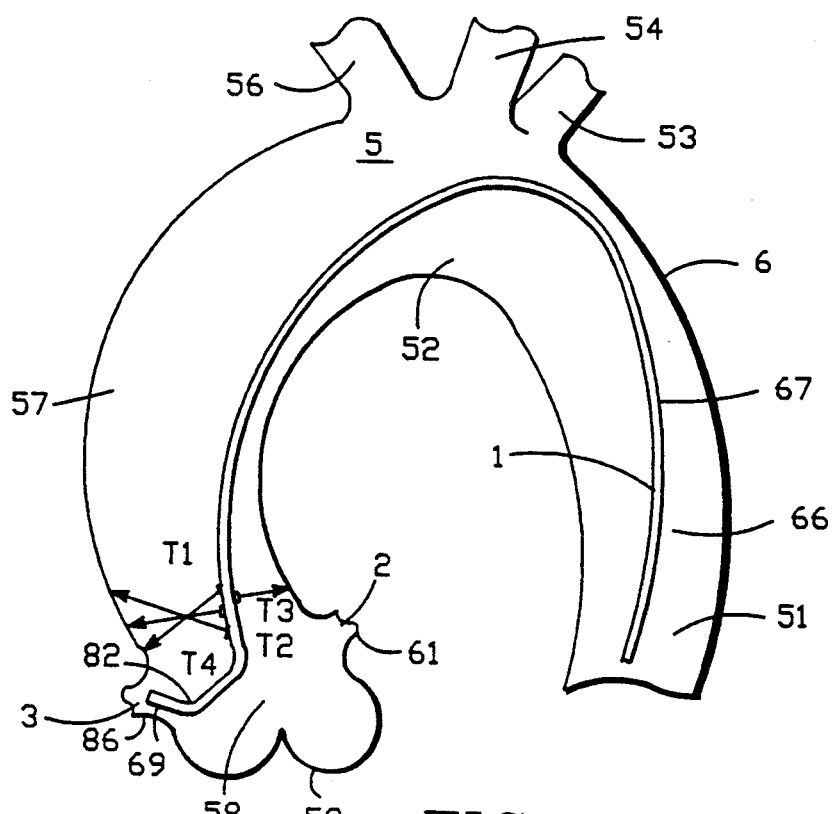
FIG. 7 is a cross-sectional view taken along the line 6—6 of FIG. 5 in which it is positioned within the heart of the heart in accordance with the present method to make volumetric measurements.

Let it be assumed that it is desired to utilize the coronary angiographic catheter 66 in connection with a diagnostic procedure of a heart of a human patient in contradistinction to the use of the guiding catheter 11 hereinbefore described, which is typically used in conjunction with an interventional procedure. As can be noted from the foregoing description, the angiographic catheter 66 is typically of a smaller size than the guiding catheter 11 and for example, ranges from 5 to 7 French. A typical use of the coronary angiography catheter 66 is shown in FIG. 7 in which the catheter 66 is introduced into the femoral artery of the patient through an introducer and thence into the descending aorta 51 over the aortic arch past the arteries 53, 54 and 56 and down into the ascending aorta 57 in proximity to the ostium 58 adjacent the aortic valve 59 and thence into the right coronary artery 86. Radiopaque dye can then be introduced through the central body 77 of the wye adapter 76 through the open end of the catheter 66 to permit visualization of flow of blood through the right coronary artery 86 in connection with conventional radiographic techniques. At the same time the volumetric blood flow in the aorta 57 can be ascertained by making diameter and velocity measurements by the use of the transducers T1, T2, T3, and T4 as described in U.S. Pat. Nos. 4,947,852 and 5,078,148. In addition and at the same time if desired, a Doppler-tipped guide wire of the type disclosed in U.S. Pat. Nos. 4,958,642 and 4,961,433 can be introduced through the angiographic catheter 66 so that its distal extremity protrudes from the distal extremity 69 of the catheter 66 to permit velocity measurements to be made directly within the right coronary artery. The Doppler-tipped guide wire can be connected to conventional instrumentation so that such velocity measurements can be made contemporaneously with the flow characteristics measurements being made in the ascending aorta 57 with the angiographic catheter 66. After the desired diagnostic procedures have been completed, the Doppler-tipped guide wire in the coronary angiographic catheter 66 can be removed to complete the procedure.

From the foregoing it can be seen that the guiding catheter 11 and the coronary angiographic catheter 66 are both positioned in the aorta 57 so that the flow characteristics measurements being made by use of the transducer T1, T2, T3 and T4 are in a location to measure substantially all of the blood flow in the aorta because they are upstream from the arteries 53, 54 and 56 at the apex of the aortic arch 52.

Also it should be appreciated that the transducer T1, T2, T3 and T4 are positioned on the catheters 11 and 66 so that they are spaced away from the area of turbulence just down stream of the aortic valve 59, one of the optimum places to measure aortic blood flow. It is in a region spaced slightly above the aortic valve 59 and upstream of the aortic arch 52 so that the transducer T1, T2, T3 and T4 are positioned in a region of well defined flow.

By ascertaining flow characteristics in the aorta of the heart, it is possible to obtain additional information about the condition of the heart and the various functions it is performing. By the present method, total blood flow or output from the ascending aorta 57 is ascertained. Thus, all of the flow coming out of the patient's heart except that blood which is flowing into the left and right coronary arteries 61 and 86 is measured.

We claim:

1. In a vascular catheter for measuring flow characteristics of a liquid in a vessel and having a vessel wall and an axis extending longitudinally of the vessel parallel to the vessel wall, a flexible elongate tubular member adapted to be introduced into the vessel and having proximal and distal extremities, said tubular member being circular in cross section and having a diameter, said flexible elongate member having a main lumen extending therethrough which is substantially ovoid in cross section and having a major axis extending across a major portion of the diameter of the tubular member, said flexible elongate member having at least one preformed bend adjacent the distal extremity, a plurality of ultrasonic transducers mounted on the flexible elongate member adjacent to said bend, said flexible elongate tubular member having first and second substantially crescent-shaped lumens therein disposed on opposite sides of the major axis of the main lumen and conductor means disposed in at least one of said substantially crescent-shaped lumens connected to said ultrasonic transducers and extending through the proximal extremity of the flexible elongate tubular member, said flexible elongate member having an opening therein in the distal extremity which is in communication with said lumen.

2. A catheter as in claim 1 where at least one additional lumen is provided in the flexible elongate tubular member for receiving the conductors connected to the ultrasonic transducers.

3. A catheter as in claim 1 wherein said catheter is a guiding catheter and is of the size ranging from 7 to 11 French.

4. A chatheter as in claim 3 wherein said flexible elongate member has a diameter ranging from 0.091" to 0.143" and wherein said main lumen has a size of approximately 0.060"×0.080".

5. A catheter as in claim 1 wherein said catheter is an angiographic catheter ranging in size from 5 to 7 French.

6. A catheter as in claim 4 wherein the flexible elongate member has a diameter of 0.065" to 0.091" and wherein said main lumen has a size of approximately 0.038"×0.060."

7. In a guiding catheter assembly, a guiding catheter for measuring flow characteristics of a liquid in a vessel and having a vessel wall and an axis extending longitudinally of the vessel parallel to the vessel wall, said guiding catheter having a flexible elongate tubular member adapted to be introduced into the vessel and having proximal and distal extremities, said tubular member being circular in cross section and having a diameter, said flexible elongate member having a main lumen extending therethrough with an opening at the distal extremity in communication with the lumen, said lumen being substantially ovoid in cross section and having a major axis extending across a major portion of the diameter of the tubular member, said flexible elongate member having at least one preformed bend adjacent the distal extremity and a plurality of ultrasonic transducers mounted on the flexible elongate member adjacent to the said bend, said flexible elongate member having first and second substantially crescent-shaped lumens therein disposed on opposite sides of the major axis of the main lumen and electrical connectors disposed in at least one of the crescent-shaped lumens and connected to said ultrasonic transducers and extending through the flexible elongate member to the proximal extremity thereof, a balloon catheter disposed in the main lumen of the guiding catheter, said balloon catheter comprising a flexible elongate member having proximal distal extremities, a balloon disposed on the distal extremity of the flexible elongate member of the balloon catheter, said flexible elongate member of the balloon catheter having a balloon inflation lumen in communication with the interior of the balloon and extending to the proximal extremity of the flexible elongate member of the balloon catheter and an additional lumen extending the length thereof and a flexible guide wire disposed in the additional lumen of the flexible elongate member of the balloon catheter.

8. A guiding catheter assembly as in claim 7 wherein said guide wire is provided with a Doppler transducer at its distal extremity together with electrical conductors disposed within the guide wire extending to the proximal extremity of the guide wire.

9. In a method for evaluating the total cardiac output flow characteristics of a heart in a human patient by the use of a flexible elongate catheter having a distal extremity having a bend thereon and a plurality of ultrasonic transducers mounted on the distal extremity in close proximity to said bend, advancing the distal extremity of the catheter into the heart and into the ascending aorta of the heart so that the ultrasonic transducers are positioned just downstream of the aortic valve to minimize turbulence to measure substantially the total blood flow from the ascending aorta.

10. A method as in claim 9 in which the blood flow is measured during systole.

* * * * *